(12) United States Patent
Gingras et al.

(10) Patent No.: US 6,315,791 B1
(45) Date of Patent: Nov. 13, 2001

(54) SELF-EXPANDING PROTHESIS

(75) Inventors: Peter H. Gingras, Windham; Theodore Karwoski, Hollis, both of NH (US); Susan Hamelin, Dracut, MA (US); Jonathan Goodwin, Nashua, NH (US)

(73) Assignee: Atrium Medical Corporation, Hudson, NH (US)

( * ) Notice: Subject to any disclaimer, the term of this patent is extended or adjusted under 35 U.S.C. 154(b) by 0 days.

(21) Appl. No.: 09/220,878

(22) Filed: Dec. 23, 1998

Related U.S. Application Data

(63) Continuation-in-part of application No. 08/759,877, filed on Dec. 3, 1996, now Pat. No. 6,010,529.

(51) Int. Cl.$^7$ .................................................. A61F 2/06
(52) U.S. Cl. ......................... 623/1.13; 623/1.2; 623/1.46
(58) Field of Search .................... 623/1.13, 1.2, 623/1.46

(56) References Cited

U.S. PATENT DOCUMENTS

| | | | |
|---|---|---|---|
| 4,733,665 | 3/1988 | Palmaz | 606/108 |
| 4,739,762 | 4/1988 | Palmaz | 606/108 |
| 4,776,337 | 10/1988 | Palmaz | 128/343 |
| 4,795,458 | 1/1989 | Regan | 623/1 |
| 4,994,066 | 2/1991 | Voss | 606/108 |
| 5,037,427 | 8/1991 | Harada et al. | 606/108 |
| 5,064,435 | 11/1991 | Porter | 623/12 |
| 5,067,957 | 11/1991 | Jervis | 606/108 |
| 5,102,417 | 4/1992 | Palmaz | 606/195 |
| 5,522,881 * | 6/1996 | Lentz | 623/1.13 |
| 5,522,882 | 6/1996 | Gaterud et al. | 623/1 |
| 5,556,414 * | 9/1996 | Turi | 623/1.13 |
| 5,562,726 | 10/1996 | Chuter | 623/1 |
| 5,591,195 * | 1/1997 | Taheri et al. | 623/1.13 |
| 5,607,467 | 3/1997 | Froix | 623/1 |
| 5,725,572 | 3/1998 | Lam et al. | 623/1 |
| 5,735,892 * | 4/1998 | Myers et al. | 623/1.13 |
| 5,741,333 | 4/1998 | Frid | 623/12 |
| 5,746,765 | 5/1998 | Kleshinski et al. | 606/198 |
| 5,772,669 | 6/1998 | Vrba | 606/108 |
| 5,788,626 | 8/1998 | Thompson | 600/36 |
| 5,788,707 | 8/1998 | Del Toro et al. | 606/108 |
| 5,797,952 | 8/1998 | Klein | 606/198 |
| 5,800,517 | 9/1998 | Anderson et al. | 623/1 |
| 5,810,870 | 9/1998 | Myers et al. | 606/198 |
| 5,824,045 | 10/1998 | Alt | 623/1 |
| 5,876,448 * | 3/1999 | Thompson et al. | 623/1.13 |
| 5,922,020 | 7/1999 | Klein et al. | 623/1 |
| 6,086,610 | 7/2000 | Duerig et al. | 623/1 |

FOREIGN PATENT DOCUMENTS

| | | |
|---|---|---|
| 3918736 | 12/1990 | (DE) . |
| 578998-B1 * | 10/1997 | (DE) . |
| WO 98/26731 | 6/1998 | (WO) . |
| WO 00/24338 | 5/2000 | (WO) . |

OTHER PUBLICATIONS

Dolmatch, B.L. et al. "Patency and Tissue Response Related to Two Types of Polytetrafluoroethylene–Covered Stents in the Dog" Journal of Vascular and Interventional Radiology 7:641–649 (1996).

* cited by examiner

*Primary Examiner*—Corrine McDermott
*Assistant Examiner*—Choon P. Koh
(74) *Attorney, Agent, or Firm*—Lahive & Cockfield, LLP

(57) ABSTRACT

An expandable prosthesis includes a self-expanding stent deployable between a substantially radially compressed configuration and a substantially radially expanded configuration. A biocompatible coating is attached to at least a portion of the outer surface of the self-expanding stent in the radially compressed configuration to inhibit radially expansion of the self-expanding stent to the radially expanded configuration. The biocompatible material is preferably integrally mounted to the self-expanding stent thus eliminating the need for a separate, independent delivery tube or sheath for maintaining the self-expanding stent in the radially compressed configuration during delivery of the self-expanding stent into a body vessel.

43 Claims, 8 Drawing Sheets

SELF-EXPANDING PROTHESIS

REFERENCE TO RELATED APPLICATIONS

This application is a continuation-in-part of U.S. patent application Ser. No. 08/759,877, filed Dec. 3, 1996 U.S. Pat. No. 6,010,529 and incorporated herein by reference.

BACKGROUND OF THE INVENTION

The present invention relates to expandable intraluminal prostheses for use in body passages, and more particularly, to self-expanding intraluminal prostheses useful for the treatment of body passages, such as blood vessels, occluded by disease.

Self-expanding prostheses are commonly used to restore and maintain the patency of body passages, particularly blood vessels. Self-expanding prostheses include stents constructed from shape memory materials, such as Nitinol, stents constructed of conventional materials, such as stainless steel, in a configuration that exhibits self expansion characteristics, and other varieties of prostheses. Such self-expanding stents can be compressed into a reduced diameter state suitable for percutaneous insertion into the body passage through a catheter. The self-expanding stent is typically held in the reduced diameter state until delivery into the body passage, whereupon the self-expanding stent is released to an increased diameter state within the body passage to hold open the body passage.

Problems associated with such conventional self-expanding stents include the need for pre-dilation of the body vessel, typically with a catheter-deployed balloon, prior to deployment of the self-expanding stent. Pre-dilation of the body vessel is necessary because the self-expanding stent alone frequently lacks sufficient radial expansion strength to completely open the diseased body vessel. Additionally, post-dilation of the self-expanding stent can be necessary to ensure the self-expanding stent has deployed to a sufficient diameter to engage the walls of the blood vessel. The need for pre- and post-dilation increases the duration of the medical procedure and the risk to the patient.

Additionally, conventional self-expanding stents generally require a separate containment system, for example a delivery tube or sheath, that radially constrains the stent in the reduced diameter state during catheter delivery and until the stent is deployed within the body vessel. Frequently, the self-expanding stent moves within the body vessel as the containment system is removed, adversely effecting the accuracy of the deployment of the stent within the body vessel. Moreover, the removal of the delivery sheath once the stent is in place requires an additional step, prolonging the medical procedure and, thus, the risk to the patient.

SUMMARY OF THE INVENTION

The present invention provides an expandable prosthesis that includes a self-expanding stent deployable between a substantially radially compressed configuration and a substantially radially expanded configuration. A biocompatible coating is attached to at least a portion of the outer surface of the self-expanding stent in the radially compressed configuration to inhibit radial expansion of the self-expanding stent to the radially expanded configuration. The biocompatible material is preferably integrally mounted to the self-expanding stent thus eliminating the need for a separate, independent containment system, such as a delivery tube or sheath, for maintaining the self-expanding stent in the radially compressed configuration during delivery of the self-expanding stent into a body vessel.

The self-expanding stent is preferably constructed from a material having shape-memory properties such as an alloy of nickel and titanium, (e.g. Nitinol). The biocompatible coating is preferably expanded polytetrafluoroethylene (ePTFE) and can extend between the first and second ends of the self-expanding stent. In addition, the biocompatible coating can be folded-over the first end and/or the second end of the self-expanding stent and can be attached to at least a portion of the inner surface of the self-expanding stent. In a preferred embodiment, the biocompatible coating is attached to the inner and outer surfaces and extends between the first and second ends of the stent to encapsulate the self-expanding stent.

In accordance with an alternative embodiment of the present invention, the expandable prosthesis includes a self-expanding stent deployable between a substantially radially compressed configuration and a substantially radially expanded configuration and a plastically deformed, expanded biocompatible coating attached to the outer surface of the self-expanding stent.

In accordance with another embodiment of the present invention, the expandable prosthesis includes a self-expanding stent having a first diameter which permits delivery of the self-expanding stent into a body passage and a second, expanded diameter suitable for treatment of the body passage. A layer of biocompatible material is attached to at least a portion of the outer surface of the self-expanding stent that is deformable between a first state sized to restrain the self-expanding stent to the first diameter, and a second, expanded state, the layer deforming to the second, expanded state upon expansion of the self-expanding stent to the second diameter by a radially, outward extending force.

A method of forming the expandable prosthesis of the present invention includes the steps of providing a self-expanding stent that is deployable between a substantially radially compressed configuration and a substantially radially expanded configuration and coating the self-expanding stent in the radially compressed configuration with a biocompatible material to retain the stent in the radially compressed configuration. Preferably, at least a portion of the outer surface of self-expanding stent is coated with the biocompatible material. Additionally, at least a portion of the inner surface of the self-expanding stent can be coated with the biocompatible material.

A method of deploying an expandable prosthesis in a body passage in accordance with the teachings of the present invention includes the steps of providing an expandable prosthesis that includes a self-expanding stent that is deployable between a substantially radially compressed configuration and a substantially radially expanded configuration. A biocompatible coating is attached to at least a portion of the outer surface of the self-expanding stent. The prosthesis is disposed on a catheter and the prosthesis and the catheter are inserted within the body passageway. The biocompatible coating retains the self-expanding stent in the radially compressed configuration in the absence of an external, radially outward force on the self-expanding stent.

In accordance with one aspect of the present invention, the prosthesis is expanded at a desired location in the body passage by applying a radially outward force on the prosthesis to place the biocompatible material into contact with the body passage. The step of expanding the prosthesis radially deforms the biocompatible coating beyond its elastic limit. The radially outward force on the prosthesis can be provided by inflating a catheter-deployed balloon within the self-expanding stent.

BRIEF DESCRIPTION OF THE DRAWINGS

These and other features and advantages of the present invention will be more fully understood by reference to the following detailed description in conjunction with the attached drawings in which like reference numerals refer to like elements through the different views. The drawings illustrate principles of the invention and, although not to scale, show relative dimensions.

DETAILED DESCRIPTION OF THE EMBODIMENTS

Figure 1:
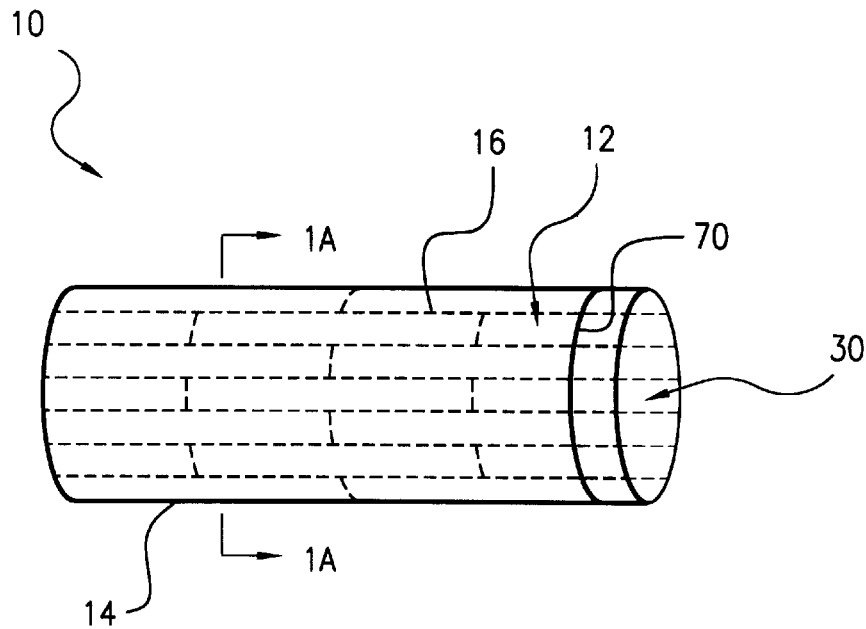
FIG. 1 is a perspective view of the expandable prosthesis of the present invention.

An expandable prosthesis 10 for restoring and maintaining the patency of body vessels, in particular blood vessels, according to the teachings of the present invention is illustrated in FIG. 1. The expandable prosthesis 10 is deployable between a substantially radially compressed configuration, suitable for insertion into the body vessel, and a substantially radially expanded configuration for treatment of the body vessel. In the radial compressed configuration the diameter of the expandable prosthesis 10 is preferable less than the diameter of the body vessel being treated. Conversely, in the expanded configuration, the diameter of the prosthesis 10 is preferable slightly greater than or equal to the diameter of the body vessel. The expandable prosthesis 10 includes a self-expanding stent 12 and a biocompatible coating 14 attached to at least a portion of the outer surface 16 of the self-expanding-stent 12.

The expandable prosthesis 10 of the present invention is particularly suited for intraluminal delivery to a body vessel. The term "intraluminal" used herein means that delivery of the prosthesis 10 occurs at a target site within a body vessel, such as a blood vessel including, for example, coronary arteries, peripheral arteries, and cerebral arteries. The prosthesis 10 and the methods of the present invention, however, are not limited to use in the vascular system, and may be also employed in other body vessels, including, for example, the prostatic urethra to treat the prostate for benign prostate hyperplasia (BPH) or prostate cancer, the fallopian tube to treat strictures, and the brain parenchyma to treat Parkinson's disease.

Figure 2A:
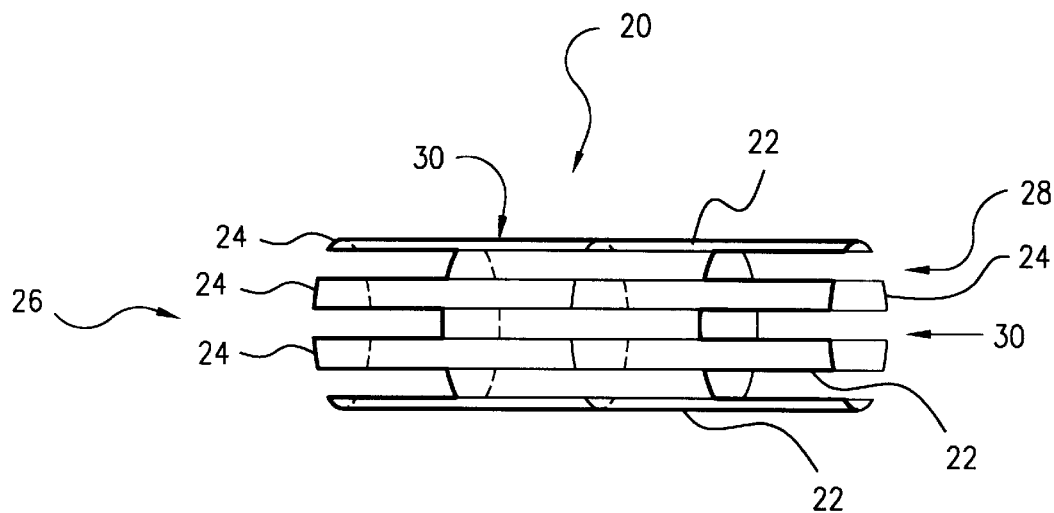
FIG. 2A is a perspective view of the self-expanding stent of the expandable prosthesis of FIG. 1; illustrating the self-expanding stent in the radially compressed configuration.
Figure 2B:
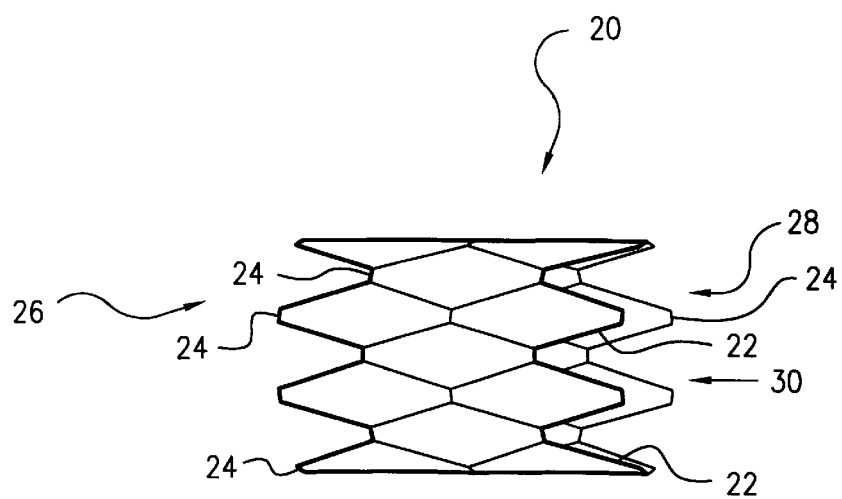
FIG. 2B is a perspective view of the self-expanding stent of the expandable prosthesis of FIG. 1, illustrating the self-expanding stent in the radially expanded configuration.

Referring to FIGS. 2A and 2B, the self-expanding stent 12 includes a skeletal frame 20 having a plurality of generally axially extending members 22 connected by a plurality of generally transverse members 24 extending substantially transverse to the longitudinal axis and to the axial members 22. The self-expanding stent 12 includes a first end 26 and a second end 28. The outer surface 16 extends between the first end 26 and the second end 28 of the stent 12. The stent 12 also includes an inner lumen 30. The self-expanding stent 12 can be deployed between a substantially compressed or crimped configuration, illustrated in FIG. 2A and a substantially radially expanded configuration, illustrated in FIG. 2B.

The self-expanding stent 12 is preferably constructed from materials which permit the size transition between the compressed and expanded configurations. Such materials include resilient polymers and special alloys that exhibit shape-memory properties or superelastic properties. Preferably, the self-expanding stent 12 is constructed from a shape-memory alloy that allows the stent 12 to deploy from the compressed configuration to the expanded configuration at slightly below mammalian body temperature, e.g. 32° C. Such shape-memory alloys include a nickel and titanium alloy commonly known as Nitinol.

Nitinol can exhibit two properties useful for the construction of stents and related medical prostheses-shape-memory and superelasticity. The primary factor for determining which of these two properties the Nitinol alloy exhibits is the austenite finish temperature ($A_f$), the temperature at which the transition of the alloy from the martensitic phase to the austenitic phase is complete. In the martensitic phase, the alloy is malleable. In the austenitic phase the alloy is resilient or superelastic. Superelasticity refers to the ability of the alloy to withstand large elastic deformations, e.g. up to 8% strain, at temperatures above the transition temperature $A_f$, but still return to the pre-constrained configuration without permanent deformation after the constraint is released.

Alternatively, a Nitinol alloy can be fabricated to exhibit shape-memory properties so that the alloy will undergo a transition from the martensitic phase to the austenitic phase, at a predetermined temperature. A Nitinol alloy stent can be fabricated to remain martensitic and in a constrained configuration below the predetermined transition temperature $A_f$ but become austenitic and expand above the transition temperature $A_f$, e.g. at the body temperature or slightly below. The formation of stents from Nitinol alloys having both superelastic and shape-memory properties is well described in the patent, scientific, and medical literature, and will not be described in detail herein.

Figure 3A:
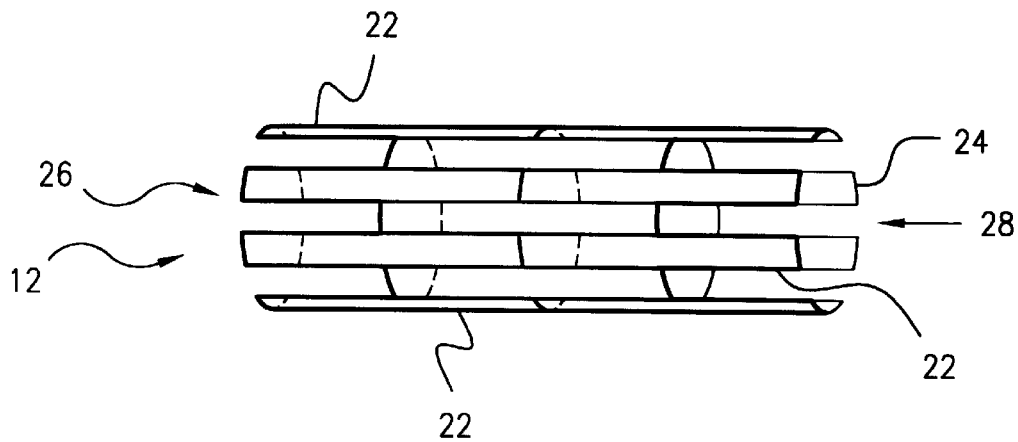
FIGS. 3A–C are perspective views of the self-expanding stent of the expandable prosthesis of FIG. 1, illustrating a method of manufacturing the self-expanding stent.
Figure 3B:
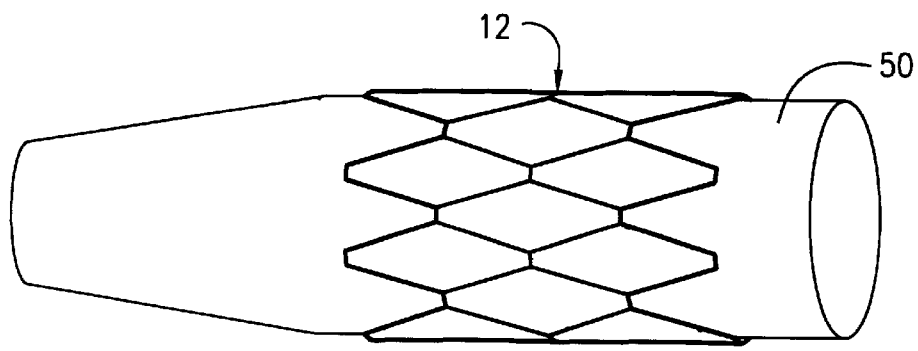
Figure 3C:
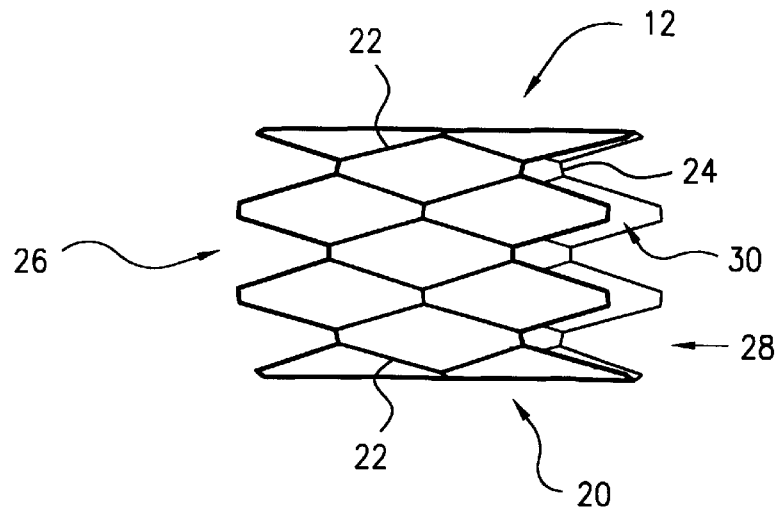
Figure 4:
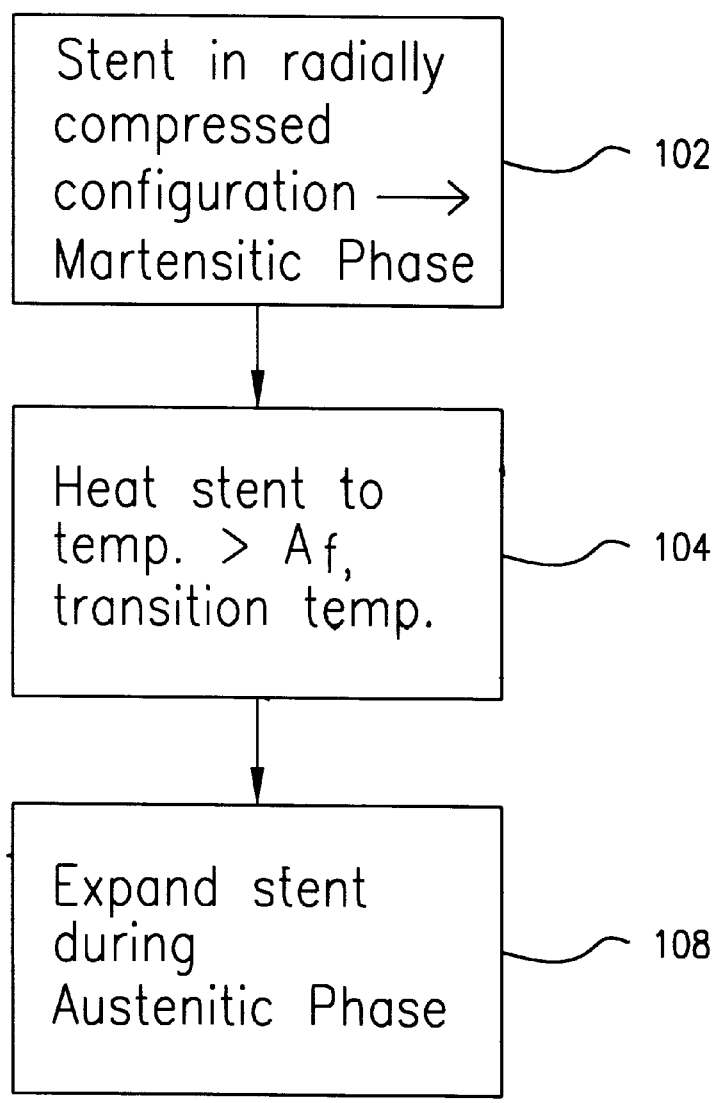
FIG. 4 is a flow chart illustrating the process of manufacturing the self-expanding stent of the expandable prosthesis of FIG. 1.

With reference to FIGS. 3A–3B and 4, an exemplary process for manufacturing a self-expanding stent constructed from a Nitinol alloy having shape-memory properties will be described. A self-expanding stent 12 is fabricated from a Nitinol alloy and is maintained in the compressed configuration while in the martensitic phase, i.e. at a temperature below the transition temperature $A_f$, as illustrated in FIG. 3A and in block 102 of FIG. 4. The self-expanding stent 12 is then heated to a temperature above the transition temperature $A_f$, so that the Nitinol alloy completely enters the austenitic phase, block 104 of FIG. 4. While in the austenitic phase, the self-expanding stent 12 is radially expanded on a tapered, stainless steel mandrel 50, as illustrated in FIG. 3B and in block 108 of FIG. 4. The self-expanding stent 12 is removed from the mandrel 50 in the expanded configuration, as shown in FIG. 3C.

A stent constructed according to this process is self-expanding and exhibits shape memory properties. While in the austenitic phase, the stent 12 is resilient and superelastic and will return to the increased diameter of the expanded configuration when deformed. Upon lowering the temperature of the stent 12 below the transition temperature $A_f$, the stent 12 enters the martensitic phase and can be transformed to the compressed configuration, as the Nitinol alloy becomes malleable. The stent 12 can maintain the reduced diameter of the compressed configuration until heated above the transition temperature $A_f$, at which point the stent 12 expands on its own to the increased diameter of the expanded configuration.

The self-expanding stent 12 of the present invention is preferably constructed of a Nitinol alloy that exhibits shape-memory properties. A Nitinol alloy is preferred because of Nitinol's flexibility, resiliency, kink-resistance, memory retention, and durability. The self-expanding stent 12 of the present invention is not limited to a Nitinol alloy construction, but can be constructed of alternative materials that exhibit resilient properties sufficient to permit the stent 12 to deploy between the compressed and expanded configurations. Additionally, the self-expanding stent 12 can be constructed of conventional alloys such as stainless steel in a configuration that exhibits self expansion characteristics. Examples of such stent include woven braided stents, such as the types described in U.S. Pat. No. 4,655,771 (Wallsten); U.S. Pat. No. 4,954,126 (Wallsten) and U.S. Pat. No. 5,061,275 (Wallsten).

The biocompatible material 14 is attached to at least a portion of the outer surface 16 of the self-expanding stent 12 in the radially compressed configuration. The term "attached" used herein means that the biocompatible material 14 is coupled to the outer surface 16 of the self-expanding stent 12 in a manner that substantially precludes removal of the biocompatible material 14 from the stent 12 under normal conditions. The biocompatible material 14 thus is an integral component of the expandable prosthesis 10 during all phases of operation of the prosthesis 10, including intraluminal introduction in the radially compressed configuration and deployment to the radially expanded configuration. The biocompatible material 14 can be attached to the outer surface 16 of the self-expanding stent12, by suturing, adhesive or thermal bonding, mechanical bonding, welding, or the like. In the alternative, the biocompatible material 14 can be configured to encapsulate portions or all of the skeletal frame 20 of the self-expanding stent 12, as discussed in detail below, to thereby inhibit radial expansion of the self-expanding stent 12.

Figure 1A:
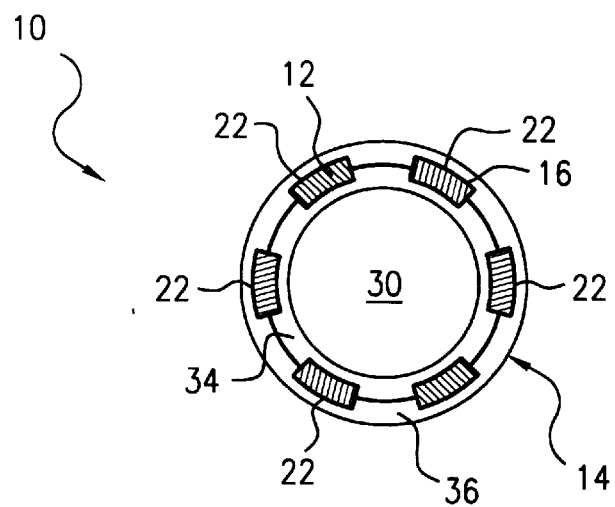
FIG. 1A is a side elevational view in cross section of the expandable prosthesis of FIG. 1, taken along the line 1A—1A of FIG. 1.

Referring to FIGS. 1 and 1A, the biocompatible coating 14 preferably extends along the outer surface 26 within the lumen 30 of the self-expanding stent 12 to completely encapsulate the stent 12 within the biocompatible coating 14. The biocompatible coating 16 includes an inner layer 34 and an outer layer 36. Preferably, the inner layer 34 and outer layer 36 are coupled together in the spaces between the axial extending members 22 and the transverse members 24. The inner and outer layers 34 and 36 can be coupled by heating the layers and applying radial pressure to the layers. The structure and process of forming the layers 34 and 36 of the biocompatible coating 14 and coupling the layers 34 and 36 to the stent 12, as well as to each other, is described in detail in commonly owned U.S. patent application Ser. No. 08/759,877, incorporated herein by reference.

The biocompatible coating 16 is preferably constructed from expanded polytetrafluoroethylene (ePTFE) or similar fluoropolymer material. Alternative fluoropolymer materials suitable for use in the present invention include, for example, polytetrafluoroethylene or copolymers of tetrafluoroethylene with other monomers may be used. Such monomers may be ethylene, chlorotrifluoroethylene, perfluoroalkoxytetrafluoroethylene, or fluorinated propylenes such as hexafluoropropylene.

The structure and process for of making ePTFE materials are described in commonly owned U.S. Pat. Nos. 5,433,909 and 5,474,824, incorporated herein by reference, and will not be described in detail herein.

Alternatively, the biocompatible coating 16 can be constructed from a bioresorbable material such as polyglycolic acid polymers, polycaprolactone polymers, polylactic acid polymers or copolymer combinations thereof.

Preferably, the biocompatible coating 16 is attached to the self-expanding stent 12 in the radially compressed configuration. The biocompatible coating 16 thus acts as an integral retaining means to inhibit radial expansion of the stent 12 to the expanded configuration, regardless of the temperature of the self-expanding stent 12. In this manner, if the temperature of the self-expanding stent 12 is raised above the transition temperature $A_f$, such that the Nitinol alloy forming the stent enters the austenitic phase, the biocompatible material coating the stent 12 restrains the stent 12 from expanding to the increased diameter of the expanded configuration.

Figure 5A:
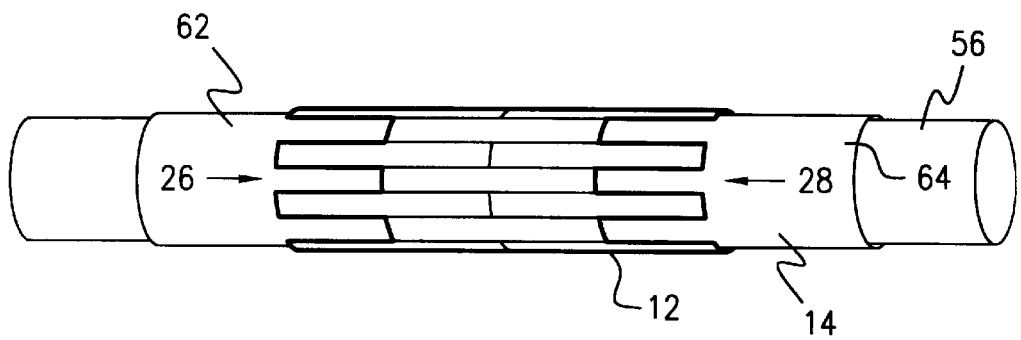
FIG. 5A is a perspective view of the self-expanding stent and the biocompatible material of the expandable prosthesis of FIG. 1, illustrating the biocompatible material positioned on a mandrel within the lumen of the self-expanding stent during the manufacturing process of the present invention.
Figure 5B:
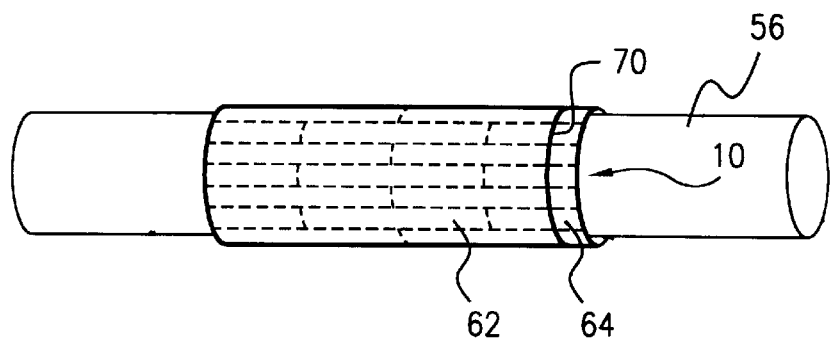
FIG. 5B is a perspective view of the expandable prosthesis of FIG. 1, illustrating the biocompatible material positioned on a mandrel and folded over the ends of the self-expanding stent to encapsulate the stent during the manufacture process of the present invention.
Figure 5C:
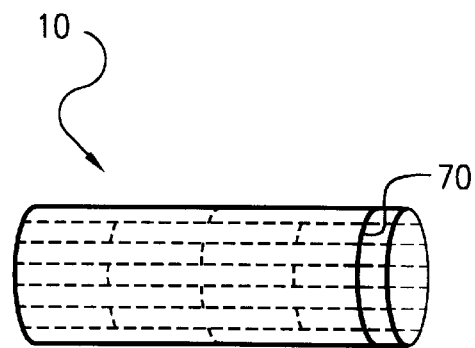
FIG. 5C is a perspective view of the expandable prosthesis of FIG. 1, illustrating the prosthesis at the completion of the manufacture process of the present invention.
Figure 6:
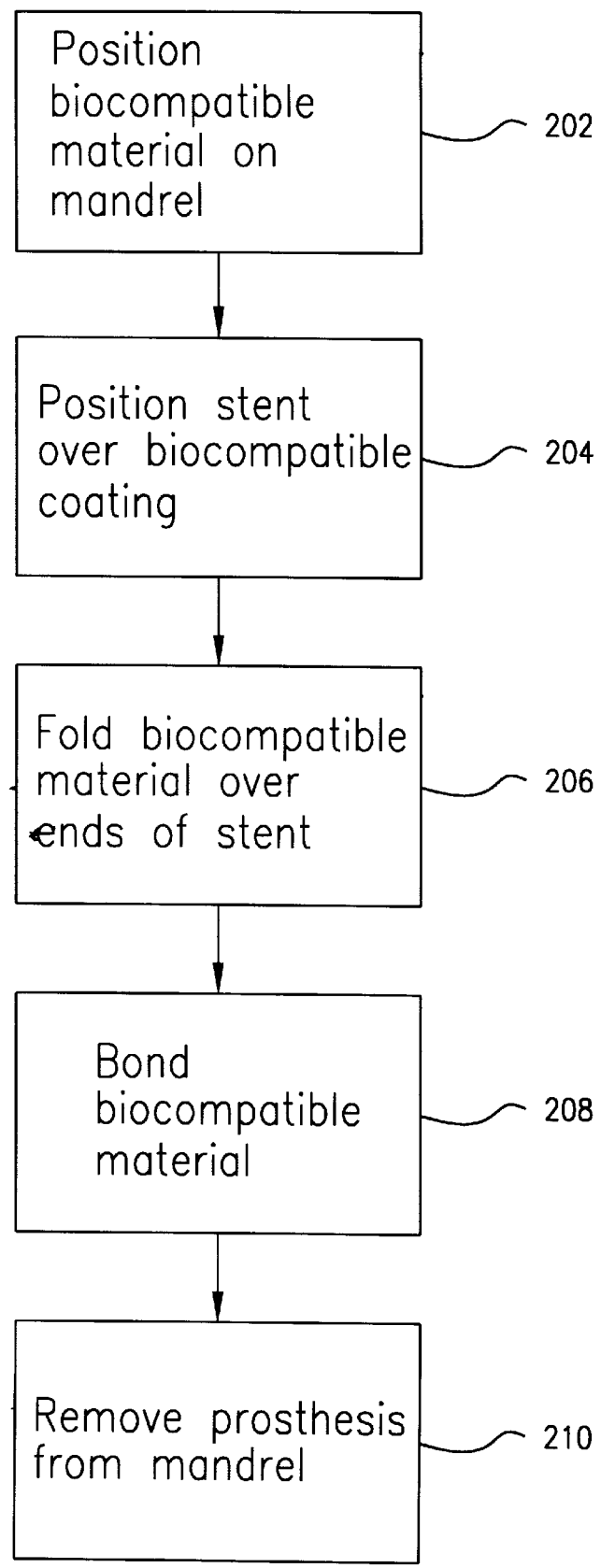
FIG. 6 is a flow chart illustrating the process of manufacturing the expandable prosthesis of FIG. 1.

Referring to FIGS. 5A–5C and 6, an exemplary method of attaching the biocompatible coating 14 to the self-expanding stent 12 to form the expandable prosthesis 10 of the present invention will be described. Initially, the biocompatible coating 14 is positioned on a cylindrical, stainless steel mandrel 56, block 202 of FIG. 6. Next, the self-expanding stent 12, in the radially compressed configuration, is positioned on the mandrel 56, over the biocompatible coating 14, such that the biocompatible coating 14 is within the lumen 30 of the stent 12, as illustrated in FIG. 5A and in block 204 of FIG. 6. End portions 62 and 64 of the biocompatible coating 14 extend out of the lumen 30 of the stent at both the first and second ends 26 and 28 of the stent 12. The end portions 62 and 64 of the biocompatible coating 14 are then folded-over the first and second ends 26 and 28, respectively, of the stent 12, block 206 of FIG. 6. The end portions 62 and 64 meet to form a single seam 70 and thus provide the outside layer 36 of the biocompatible coating 14 on the outside surface 14 of the stent 12, as shown in FIG. 5B. The seam 70 preferably does not extend from the outside layer 36 completely through the inside layer 34. The expandable prosthesis 10 is heated to cause the outside layer 36 to shrink and coalesce with the inner layer 34 together about the stent 12, block 208. Preferably, the outer and inner layers 34 and 36 bond together at all points at which the layers contact so that the two layers form a unitary and non-delaminating cocoon surrounding the stent 12. Upon completion of the heating step, the expandable prosthesis 10 is removed from the mandrel 56, block 210. The completed expandable prosthesis 10 is shown in FIG. 5C.

Figure 7A:
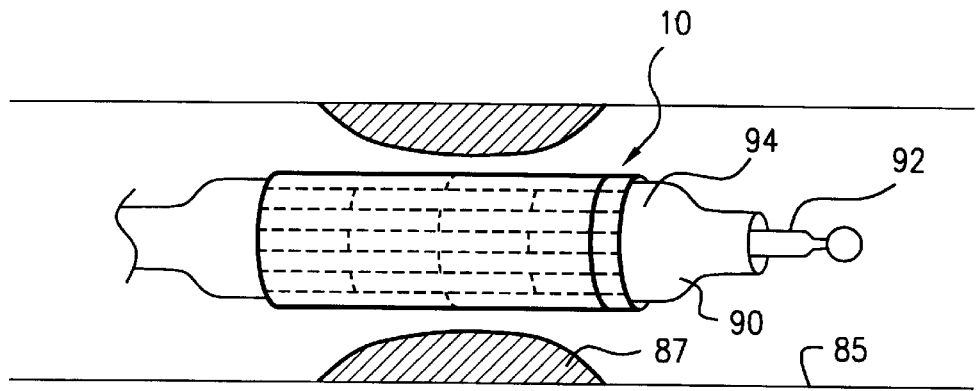
FIG. 7A is a side elevational view of the expandable prosthesis of FIG. 1, illustrating the expandable prosthesis positioned on a balloon catheter within a body vessel and in a radially compressed configuration.
Figure 7B:
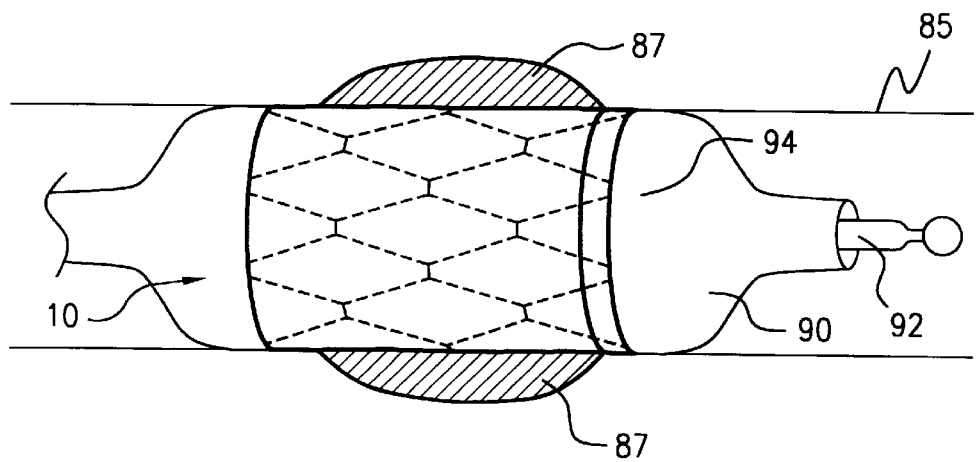
FIG. 7B is a side elevational view of the expandable prosthesis of FIG. 1, illustrating the expandable prosthesis positioned on a balloon catheter within a body vessel and in a radially expanded configuration.
Figure 8:
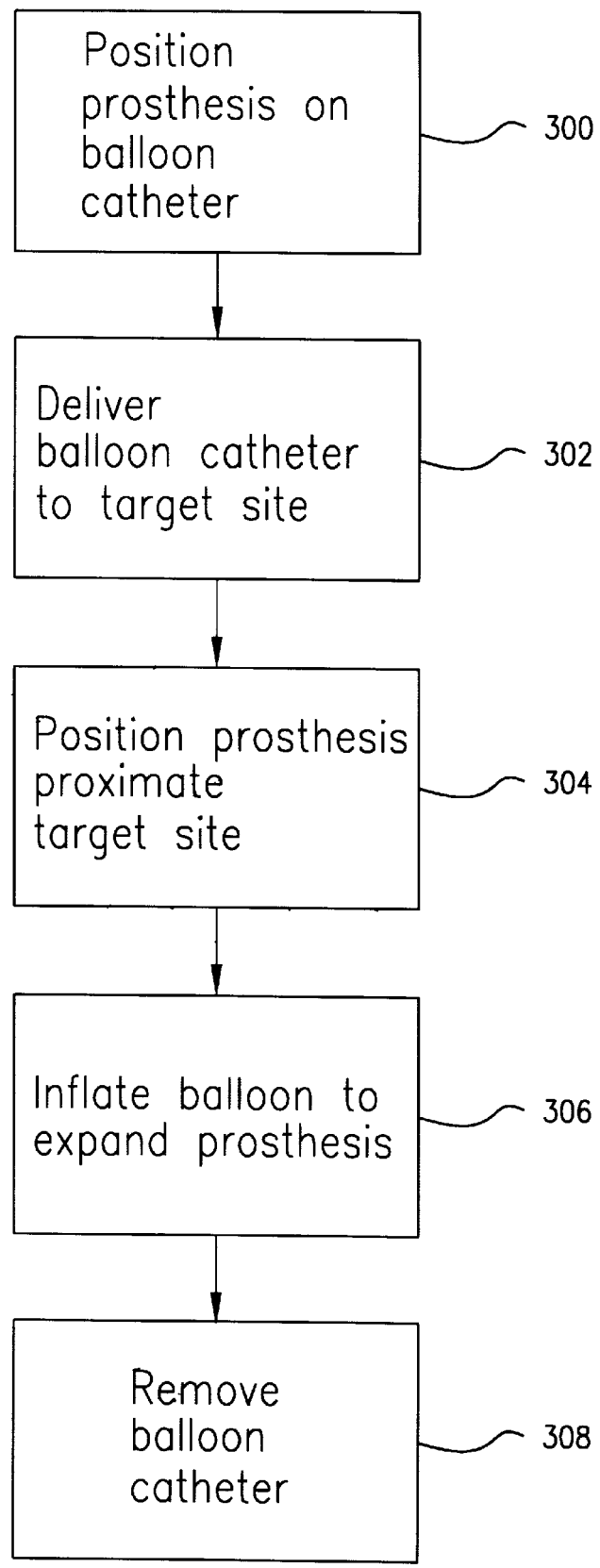
FIG. 8 is a flow chart illustrating a method of deploying the expandable prosthesis of FIG. 1 within a body vessel according to the teachings of the present invention.

A method of deploying the expandable prosthesis 10 of the present invention within a body passage is illustrated in FIGS. 7A and 7B and in connection with the flow chart of FIG. 8. Initially, the expandable prosthesis 10 of the present invention is positioned on a suitable intraluminal delivery instrument, such as a balloon catheter 90, block 300 of FIG. 8. Intraluminal balloon catheters are well described in the patent, scientific, and medical literature, and will not be described in detail herein.

The expandable prosthesis 10 is positioned on the balloon catheter 90 with the self-expanded stent 12 in the radially compressed configuration. As discussed above, it is preferable for the transition temperature $A_f$ of the Nitinol alloy forming the self-expanding stent 12 to be slightly less than the body temperature of the patient, e.g. 32° C. Thus, when the expandable prosthesis 10 is inserted into the body vessel, the Nitinol alloy enters the austenitic phase and becomes flexible and resilient. The biocompatible coating 16, however, operates as an integrally mounted retaining means, inhibiting the self-expanding stent 12 from expanding to the expanded configuration, in the absence of an external, radially outward force on the stent. Accordingly, the biocompatible coating 16 eliminates the need for a separate, independent containment system, such as a delivery tube or sheath, to maintain the self-expanding stent 12 in the compressed configuration during delivery to the treatment site within the body vessel.

Next, the balloon catheter 90 is inserted into a body vessel, such as a blood vessel 85, over a guide wire 92 and positioned proximate a target site for treatment of the body vessel, as shown in FIG. 7A and block 302 FIG. 8. The "target site" within the body vessel can be a diseased region of the body vessel, such as a stenotic region of the body vessel. In the case of blood vessels, the target site can be a region of the blood vessel 90 that is occluded by arterial plaque 87.

The balloon catheter 90 is then positioned such that the expandable prosthesis 10 is adjacent the target site, block 304 of FIG. 8. Next, the balloon 96 of the balloon catheter 90 is inflated to provide a radially-outward force on the expandable prosthesis 10, expanding the prosthesis 10 to the increased diameter of the expanded configuration, as shown in FIG. 7B and in block 306 of FIG. 8. The expandable prosthesis 10, in the expanded configuration engages the walls of the body vessel to effectively restore and maintain the patency of the occluded body vessel. Once the prosthesis 10 is expanded, the balloon 94 can be deflated and the balloon catheter withdrawn from the body vessel, block 308.

Preferably, the balloon 94 expands the expandable prosthesis 10 such that the biocompatible coating 16 expands beyond the elastic limits of the material forming the biocompatible coating 14, while concomitantly maintaining the material forming the self-expanding stent 12 within its elastic limits. By maintaining the stent 12 material within its elastic limits, the stent 12 remains flexible and resilient. The flexibility and resilient properties of the stent 12 are important for permitting the stent to accommodate motion of the body vessel and tissue surrounding the body vessel without fracturing or separating from the walls of the body vessel.

It will thus be seen that the invention efficiently attains the objects made apparent from the preceding description. Since certain changes may be made in the above constructions without departing from the scope of the invention, it is intended that all matter contained in the above description or shown in the accompanying drawings be interpreted as illustrative and not in a limiting sense.

It is also to be understood that the following claims are to cover all generic and specific features of the invention described herein, and all statements of the scope of the invention which, as a matter of language, might be said to fall therebetween.

Having described the invention, what is claimed as new and desired to be secured by Letters Patent is:

1. An expandable prosthesis comprising:
   a self-expanding stent deployable between a substantially radially compressed configuration and a substantially radially expanded configuration, the self-expanding stent including a first and a second end and an outer surface extending therebetween, and
   a biocompatible coating completely encapsulating the self-expanding stent in the radially compressed configuration to inhibit radial expansion of the self-expanding stent to the radially expanded configuration.

2. The prosthesis of claim 1, wherein the self-expanding stent is constructed from a material having shape-memory properties.

3. The prosthesis of claim 2, wherein the material having shape-memory properties is an alloy of nickel and titanium.

4. The prosthesis of claim 3, wherein the nickel and titanium alloy is Nitinol.

5. The prosthesis of claim 1, wherein the biocompatible coating is expanded polytetrafluoroethylene (ePTFE).

6. The prosthesis of claim 1, wherein the biocompatible coating extends between the first and second ends of the self-expanding stent.

7. The prosthesis of claim 1, wherein the self-expanding stent includes an inner surface, and
   wherein the biocompatible coating is folded-over the first end of the self-expanding stent and is attached to at least a portion of the inner surface of the self-expanding stent.

8. The prosthesis of claim 1, wherein the self-expanding stent includes an inner surface extending between the first and second ends, and
   wherein the biocompatible coating is attached to the inner and outer surfaces and extends between the first and second ends to encapsulate the self-expanding stent.

9. A prosthesis comprising:
   a self-expanding stent deployable between a substantially radially compressed configuration and a substantially radially expanded configuration, the self-expanding stent including a first and a second end and an outer surface extending therebetween, and
   means for retaining the self-expanding stent in the radially compressed configuration, the retaining means being integrally mounted to the self-expanding stent in the radially compressed configuration.

10. The prosthesis of claim 9, wherein the self-expanding stent is constructed from a material having shape-memory properties.

11. The prosthesis of claim 10, wherein the material having shape-memory properties is an alloy of nickel and titanium.

12. The prosthesis of claim 11, wherein the nickel and titanium alloy is Nitinol.

13. The prosthesis of claim 9, wherein the retaining means is a biocompatible coating completely encapsulating the self-expanding stent.

14. The prosthesis of claim 13, wherein the biocompatible coating is expanded polytetrafluoroethylene (ePTFE).

15. The prosthesis of claim 13, wherein the biocompatible coating extends between the first and second ends of the self-expanding stent.

16. The prosthesis of claim 13, wherein the self-expanding stent includes an inner surface, and
wherein the biocompatible coating is folded-over the first end of the self-expanding stent and is attached to at least a portion of the inner surface of the self-expanding stent.

17. The prosthesis of claim 13, wherein the self-expanding stent includes an inner surface extending between the first and second ends, and
wherein the biocompatible coating is attached to the inner and outer surfaces and extends between the first and second ends to encapsulate the self-expanding stent.

18. An expandable prosthesis comprising:
a self-expanding stent deployable between a substantially radially compressed configuration and a substantially radially expanded configuration, the self-expanding stent including a first and a second end and an outer surface extending therebetween, and
a biocompatible coating completely encapsulating the self-expanding stent, the biocompatible coating hindering the expansion of the self-expanding stent and capable of being plastically deformed.

19. An expandable prosthesis comprising:
a self-expanding stent having a first and a second end and an outer surface extending therebetween, the self-expanding stent having a first diameter which permits delivery of the self-expanding stent into a body passage, and a second, expanded diameter suitable for treatment of the body passage, and
layer of biocompatible material completely encapsulating the self-expanding stent, the layer being deformable between a first state sized to restrain the self-expanding stent to the first diameter, and a second, expanded state, the layer deforming to the second, expanded state upon expansion of the self-expanding stent to the second diameter by a radially, outward extending force.

20. The prosthesis of claim 19, wherein the layer of biocompatible material is expanded beyond its elastic limit during deformation to the second, expanded state so that the biocompatible material is plastically deformed.

21. The prosthesis of claim 19, wherein the self-expanding stent is constructed from a material having shape-memory properties.

22. The prosthesis of claim 21, wherein the material having shape-memory properties is an alloy of nickel and titanium.

23. The prosthesis of claim 22, wherein the nickel and titanium alloy is Nitinol.

24. The prosthesis of claim 19, wherein the biocompatible material is expanded polytetrafluoroethylene (ePTFE).

25. The prosthesis of claim 19, wherein the layer of biocompatible material extends between the first and second ends of the self-expanding stent.

26. The prosthesis of claim 19, wherein the self-expanding stent includes an inner surface, and
wherein the prosthesis further comprises a second layer of biocompatible material attached to the inner surface of the self-expanding stent.

27. A method of forming an expandable prosthesis, the method comprising the steps of:
providing a self-expanding stent having first and second ends and outer and inner surfaces extending therebetween, the self-expanding stent being deployable between a substantially radially compressed configuration and a substantially radially expanded configuration, and
coating and, completely encapsulating the self-expanding stent in the radially compressed configuration with a biocompatible material to retain the stent in the radially compressed configuration.

28. The method of claim 27, wherein the self-expanding stent is constructed from a material having shape-memory properties.

29. The method of claim 28, wherein the material having shape-memory properties is an alloy of nickel and titanium.

30. The method of claim 29, wherein the nickel and titanium alloy is Nitinol.

31. The method of claim 27, wherein the biocompatible coating is expanded polytetrafluoroethylene (ePTFE).

32. The method of claim 27, wherein the step of coating further includes the step of coating the outer surface of the self-expanding stent from the first end to the second end of the stent.

33. A method of introducing an expandable prosthesis into a body passage, the method comprising the steps of:
providing an expandable prosthesis including
a self-expandable stent having a first and a second end and an outer surface extending therebetween and being deployable between a substantially radially compressed configuration and a substantially radially expanded configuration, and
a biocompatible coating completeing encapsulating the self-expanding stent and hindering the radial expandsion of the self-expanding stent,
disposing the prosthesis on a catheter,
inserting the prosthesis and the catheter within the body passageway, the biocompatible coating retaining the self-expanding stent in the radially compressed configuration.

34. The method of claim 33, wherein the self-expanding stent is constructed from a material having shape-memory properties.

35. The method of claim 34, wherein the material having shape-memory properties is an alloy of nickel and titanium.

36. The method of claim 35, wherein the nickel and titanium alloy is Nitinol.

37. The method of claim 33, wherein the biocompatible coating is expanded polytetrafluoroethylene (ePTFE).

38. A method of deploying an expandable prosthesis in a body passage, the method comprising the steps of:
providing an expandable prosthesis including
self-expanding stent having a first and a second end and an outer surface extending therebetween, and
a biocompatible coating completely encapsulating the self-expanding stent and hindering the radial expansion of the self-expanding stent,
disposing the prosthesis on a catheter,
inserting the prosthesis and the catheter within the body passageway, and expanding the prosthesis at a desired location in the body passage by applying a radially outward force on the prosthesis to place the biocompatible material into contact with the body passage, the step of expanding and radially deforming the biocompatible coating beyond its elastic limit.

39. The method of claim 38, wherein the self-expanding stent is constructed from a material having shape-memory properties.

40. The method of claim 39, wherein the material having shape-memory properties is an alloy of nickel and titanium.

41. The method of claim 40, wherein the nickel and titanium alloy is Nitinol.

42. The method of claim 38, wherein the biocompatible coating is expanded polytetrafluoroethylene (ePTFE).

43. The method of claim 38, further comprising the step of providing the radially outward force on the prosthesis by inflating a catheter-deployed balloon within the self-expanding stent.

* * * * *

UNITED STATES PATENT AND TRADEMARK OFFICE
CERTIFICATE OF CORRECTION

PATENT NO. : 6,315,791 B1
DATED : November 13, 2001
INVENTOR(S) : Gingras et al.

It is certified that error appears in the above-identified patent and that said Letters Patent is hereby corrected as shown below:

Column 6,
Line 2, replace "surface 26 within" with -- surface 26 and within --;

Column 9,
Line 40, replace "layer of biocompatible" with -- a layer of biocompatible --.;

Column 10,
Line 12, replace "coating and, completely" with -- coating and completely --;
Line 40, replace "radial expandsion" with -- radial expansion --.
Line 60, replace "self-expanding" with -- a self-expanding --.

Signed and Sealed this

Ninth Day of July, 2002

Attest:

Attesting Officer

JAMES E. ROGAN
Director of the United States Patent and Trademark Office